US009241729B2

(12) United States Patent
Kuntz et al.

(10) Patent No.: US 9,241,729 B2
(45) Date of Patent: Jan. 26, 2016

(54) DEVICE TO AID IN THE DEPLOYMENT OF A SHAPE MEMORY INSTRUMENT

(71) Applicant: DePuy Synthes Products, Inc., Raynham, MA (US)

(72) Inventors: Kyle Kuntz, West Chester, PA (US); Marc Mueller, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 29 days.

(21) Appl. No.: 13/714,601

(22) Filed: Dec. 14, 2012

(65) Prior Publication Data

US 2014/0172000 A1   Jun. 19, 2014

(51) Int. Cl.
*A61B 17/32*   (2006.01)
*A61B 17/16*   (2006.01)
(Continued)

(52) U.S. Cl.
CPC ..... *A61B 17/320016* (2013.01); *A61B 17/1642* (2013.01); *A61B 17/1671* (2013.01); *A61B 17/885* (2013.01); *A61B 2017/00331* (2013.01); *A61B 2017/00867* (2013.01); *A61B 2017/320044* (2013.01); *A61B 2017/320056* (2013.01)

(58) Field of Classification Search
CPC .................... A61B 17/320016; A61B 17/885; A61B 17/8852; A61B 17/8855; A61B 17/8858; A61B 17/88; A61B 17/8805; A61B 17/8819; A61B 17/3421; A61B 17/3472; A61B 17/3417; A61B 2017/320056; A61B 2017/349; A61B 2017/347; A61B 2017/0046; A61B 2017/320044; A61M 2025/0004; A61M 2025/0006; A61M 25/00; A61M 25/0014

USPC ......... 606/184, 185, 167, 170, 172, 191, 279, 606/93, 190; 623/17.12, 17.11; 604/103.03, 604/117, 164.1, 164.12, 164.01, 170.03
See application file for complete search history.

(56) References Cited

U.S. PATENT DOCUMENTS

| 4,630,616 A | 12/1986 | Tretinyak |
| 5,030,201 A | 7/1991 | Palestrant |
| 5,509,923 A | 4/1996 | Middleman et al. |

(Continued)

FOREIGN PATENT DOCUMENTS

| AU | 764518 | 8/2003 |
| CA | 2327702 | 10/1999 |

(Continued)

OTHER PUBLICATIONS

Edeland, H. G., "Open reduction of central compression fractures of the tibial plateau. Preliminary report of a new method and device arrangement," Acta Orthop. Scand., Dec. 1976, 47(6), 686-689.

(Continued)

*Primary Examiner* — Jocelin Tanner
(74) *Attorney, Agent, or Firm* — Baker & Hostetler LLP

(57) ABSTRACT

A system is configured to create or enlarge a cavity in a tissue body and generally includes a cannula, a friction reduction covering, and a cavity creation member. The cavity creation member includes an end portion that is configured to transition between a first shape and a second shape that is different from the first shape. In operation, retracting the friction reduction covering relative to end portion causes the end portion to change shape from the first shape to the second shape such that the cavity creation member is configured to create or enlarge a cavity in the tissue body as the second end portion exits the friction reduction member.

25 Claims, 15 Drawing Sheets

(51) Int. Cl.
*A61B 17/88* (2006.01)
*A61B 17/00* (2006.01)

(56) References Cited

U.S. PATENT DOCUMENTS

| | | | |
|---|---|---|---|
| 5,512,037 A | 4/1996 | Russell et al. | |
| 5,709,697 A | 1/1998 | Ratcliff et al. | |
| 5,749,879 A | 5/1998 | Middleman et al. | |
| 5,904,690 A | 5/1999 | Middleman et al. | |
| 6,019,776 A | 2/2000 | Preissman et al. | |
| 6,033,411 A | 3/2000 | Preissman | |
| 6,231,615 B1 | 5/2001 | Preissman | |
| 6,241,734 B1 | 6/2001 | Scribner et al. | |
| 6,309,420 B1 | 10/2001 | Preissman | |
| 6,348,055 B1 | 2/2002 | Preissman | |
| 6,383,190 B1 | 5/2002 | Preissman | |
| 6,440,138 B1 | 8/2002 | Reiley et al. | |
| 6,676,665 B2 | 1/2004 | Foley et al. | |
| 6,679,886 B2 | 1/2004 | Weikel et al. | |
| 6,746,451 B2 | 6/2004 | Middleton et al. | |
| 6,783,515 B1 | 8/2004 | Miller et al. | |
| 6,863,672 B2 | 3/2005 | Reiley et al. | |
| 6,875,219 B2 | 4/2005 | Arramon et al. | |
| 6,923,813 B2 * | 8/2005 | Phillips et al. | 606/86 R |
| 7,048,743 B2 | 5/2006 | Miller et al. | |
| 7,476,226 B2 | 1/2009 | Weikel et al. | |
| 7,510,579 B2 | 3/2009 | Preissman | |
| 7,572,263 B2 | 8/2009 | Preissman | |
| 7,879,038 B2 | 2/2011 | Reiley et al. | |
| 7,909,827 B2 | 3/2011 | Reiley et al. | |
| 2002/0151927 A1 | 10/2002 | Douk et al. | |
| 2003/0004537 A1 | 1/2003 | Boyle et al. | |
| 2003/0187445 A1 * | 10/2003 | Keith et al. | 606/72 |
| 2003/0191474 A1 | 10/2003 | Cragg et al. | |
| 2004/0267269 A1 | 12/2004 | Middleton et al. | |
| 2006/0095049 A1 * | 5/2006 | Zannis et al. | 606/102 |
| 2007/0043430 A1 | 2/2007 | Stinson | |
| 2008/0208255 A1 | 8/2008 | Siegal | |
| 2009/0069850 A1 | 3/2009 | Fuerderer | |
| 2010/0241123 A1 | 9/2010 | Middleton et al. | |
| 2011/0276001 A1 * | 11/2011 | Schultz et al. | 604/164.01 |
| 2012/0226301 A1 * | 9/2012 | Geist | 606/172 |

FOREIGN PATENT DOCUMENTS

| | | |
|---|---|---|
| CN | 2308388 | 2/1999 |
| EP | 681811 | 11/1995 |
| EP | 1073371 B2 | 7/2009 |
| GB | 629824 | 9/1949 |
| WO | WO 00/33909 A1 | 6/2000 |
| WO | WO 2010/008818 A1 | 1/2010 |
| WO | WO 2012/071464 | 5/2012 |

OTHER PUBLICATIONS

Olerud et al., "Transpedicular fixation of thoracolumbar vertebral fractures," Clin. Orthop. Related Research, Feb. 1988, 227, 44-51.

* cited by examiner

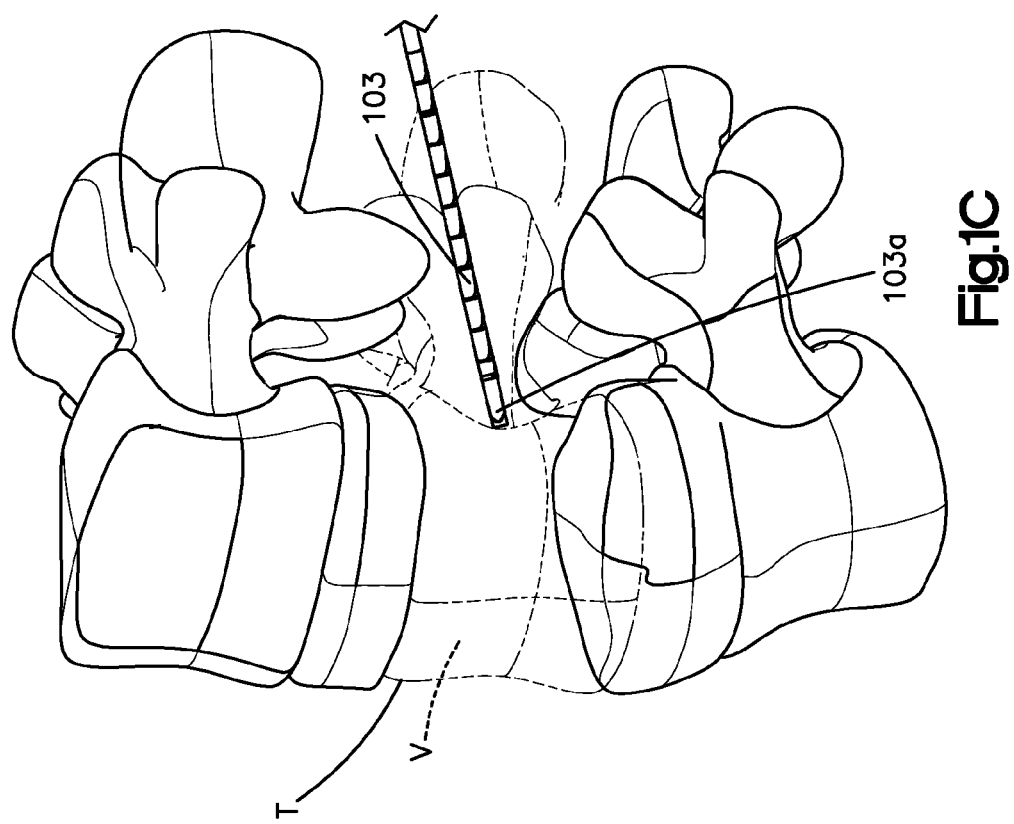

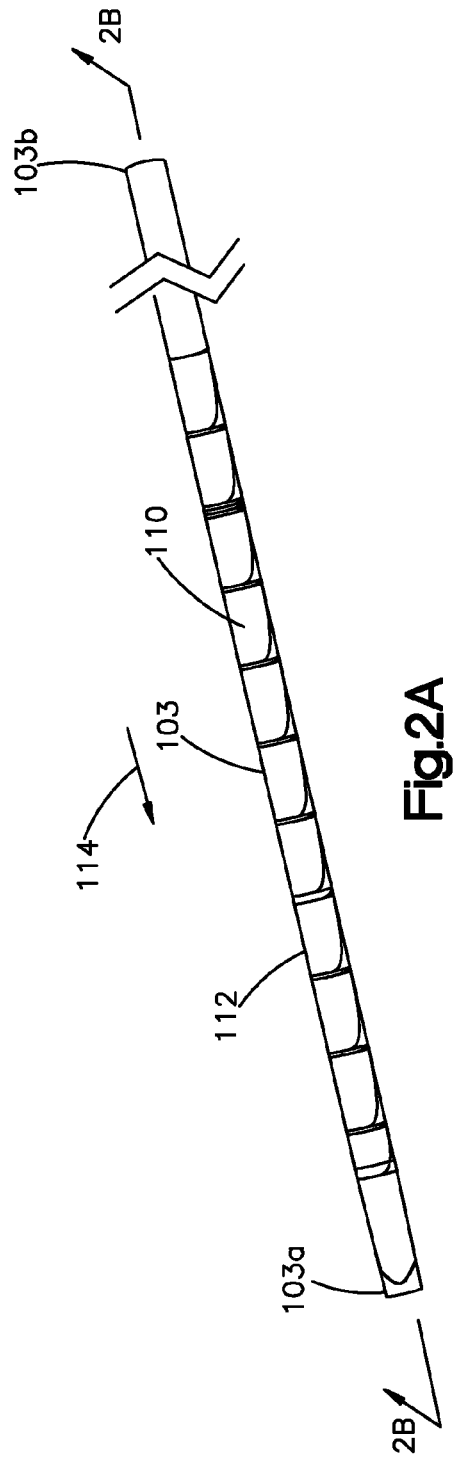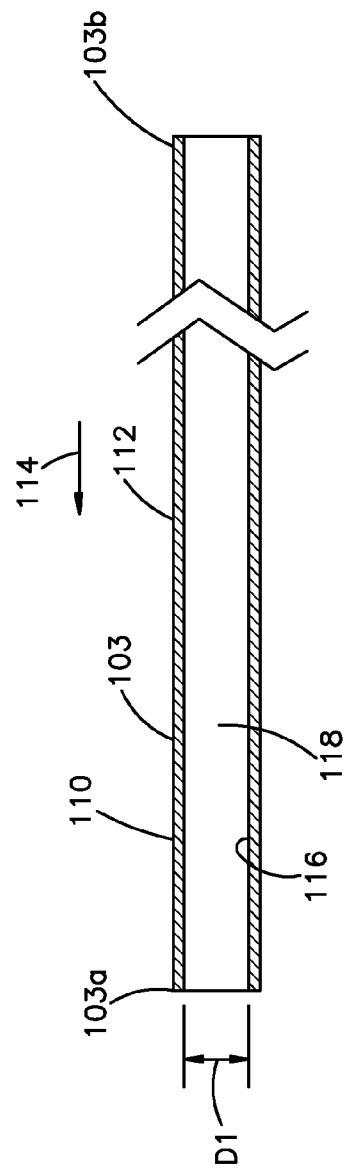

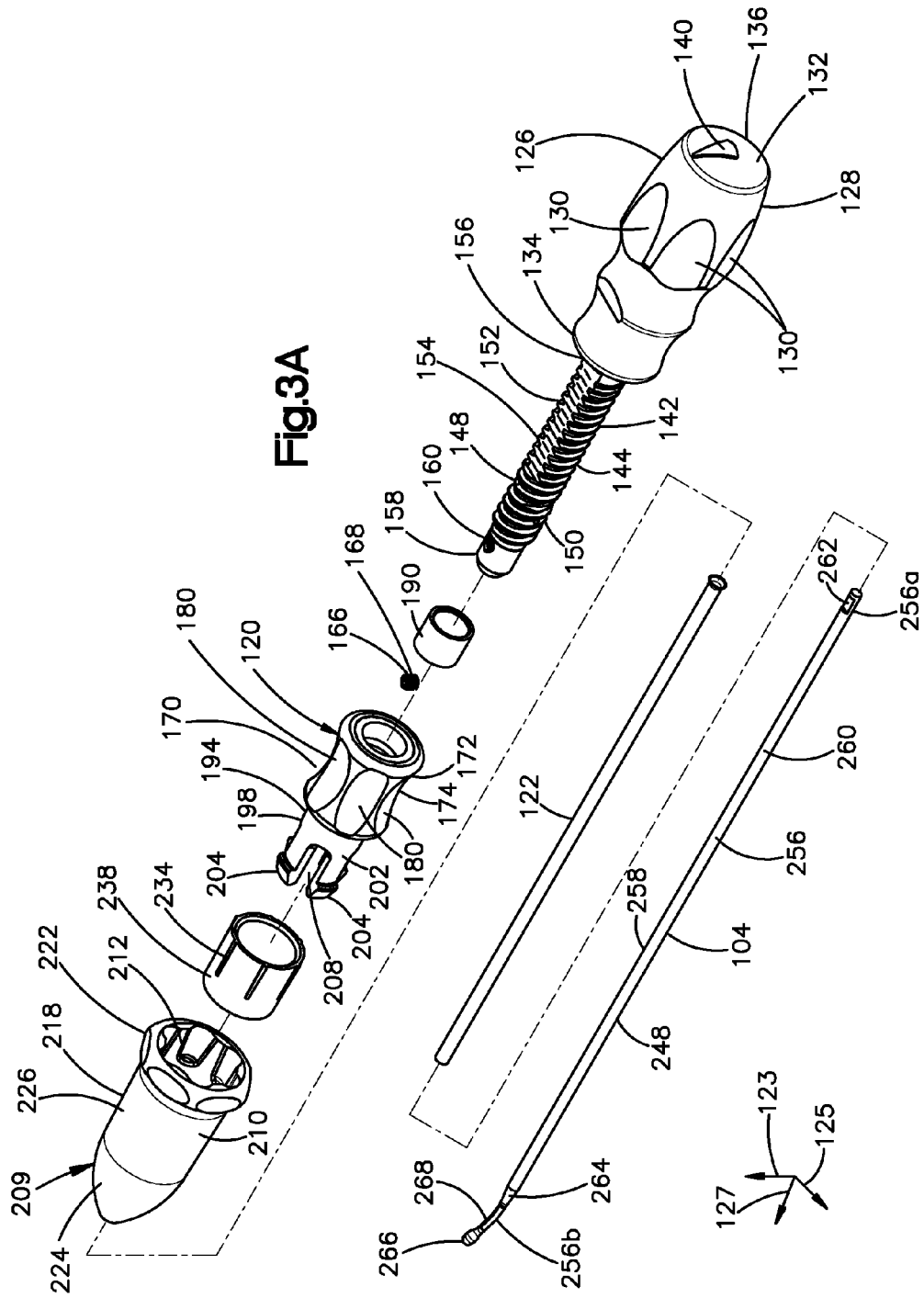

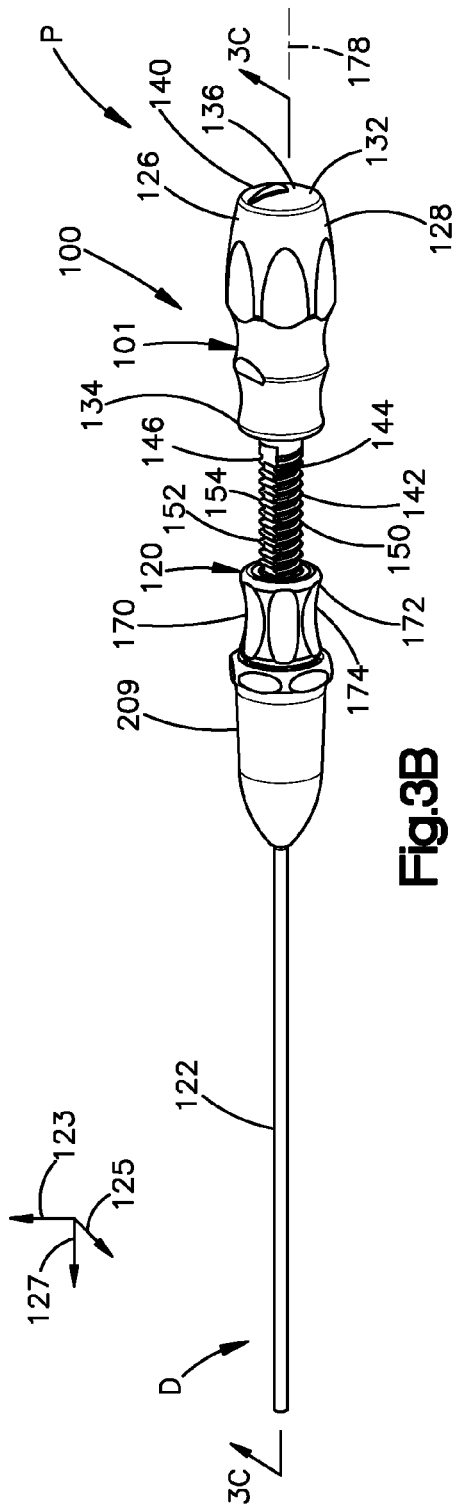
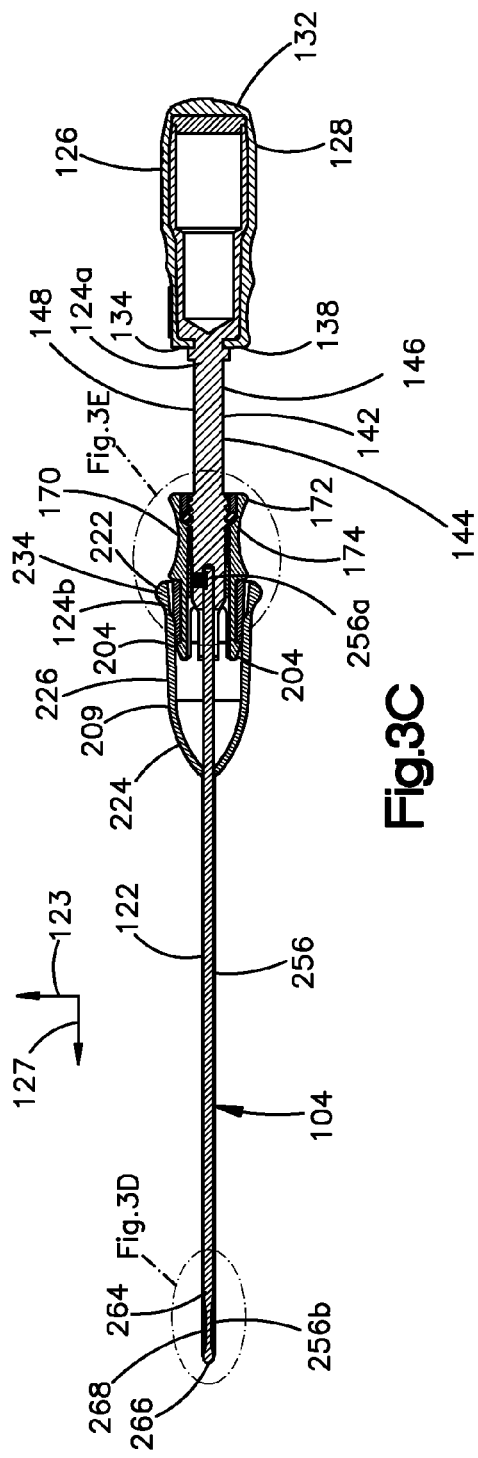
Fig.3B
Fig.3C

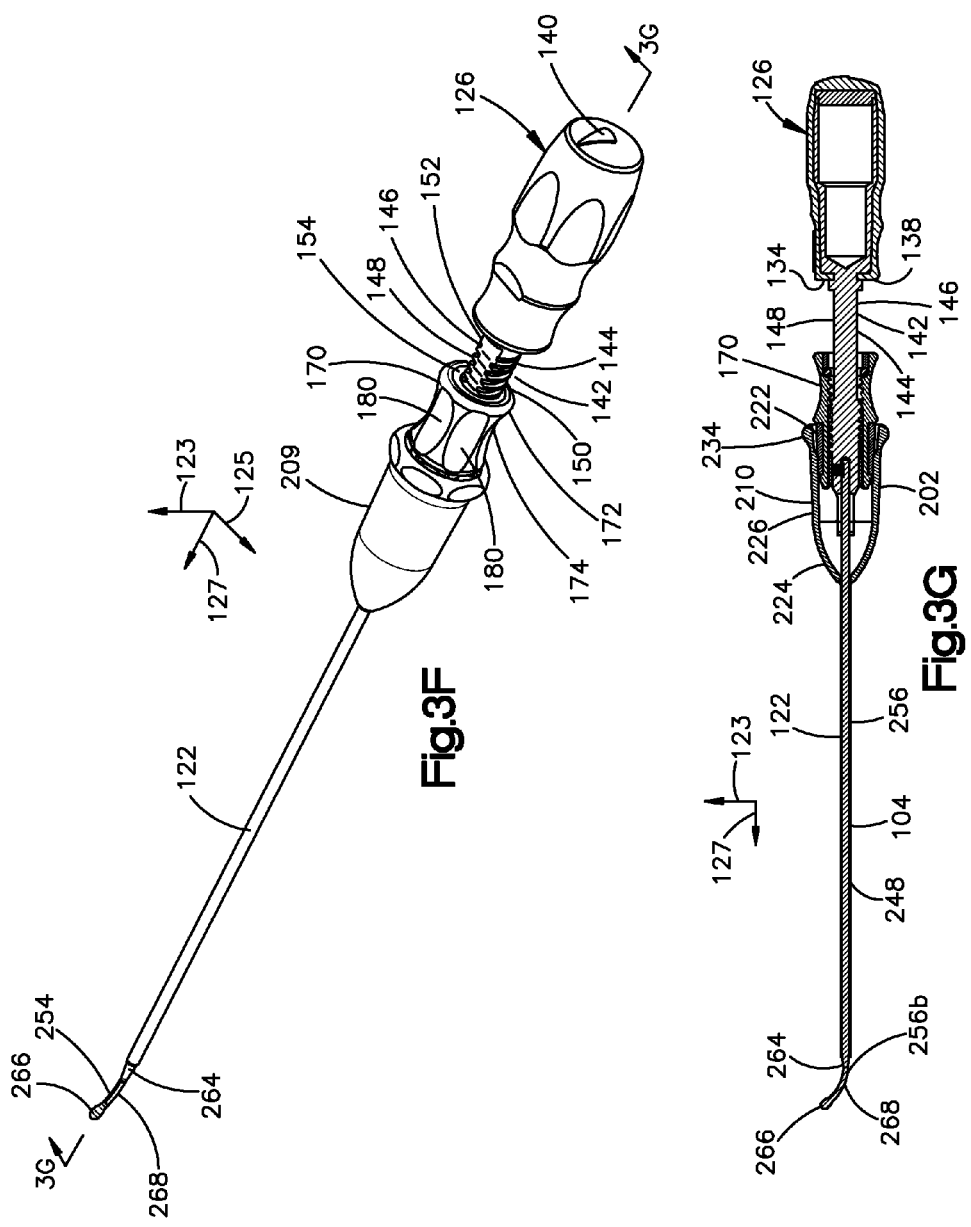

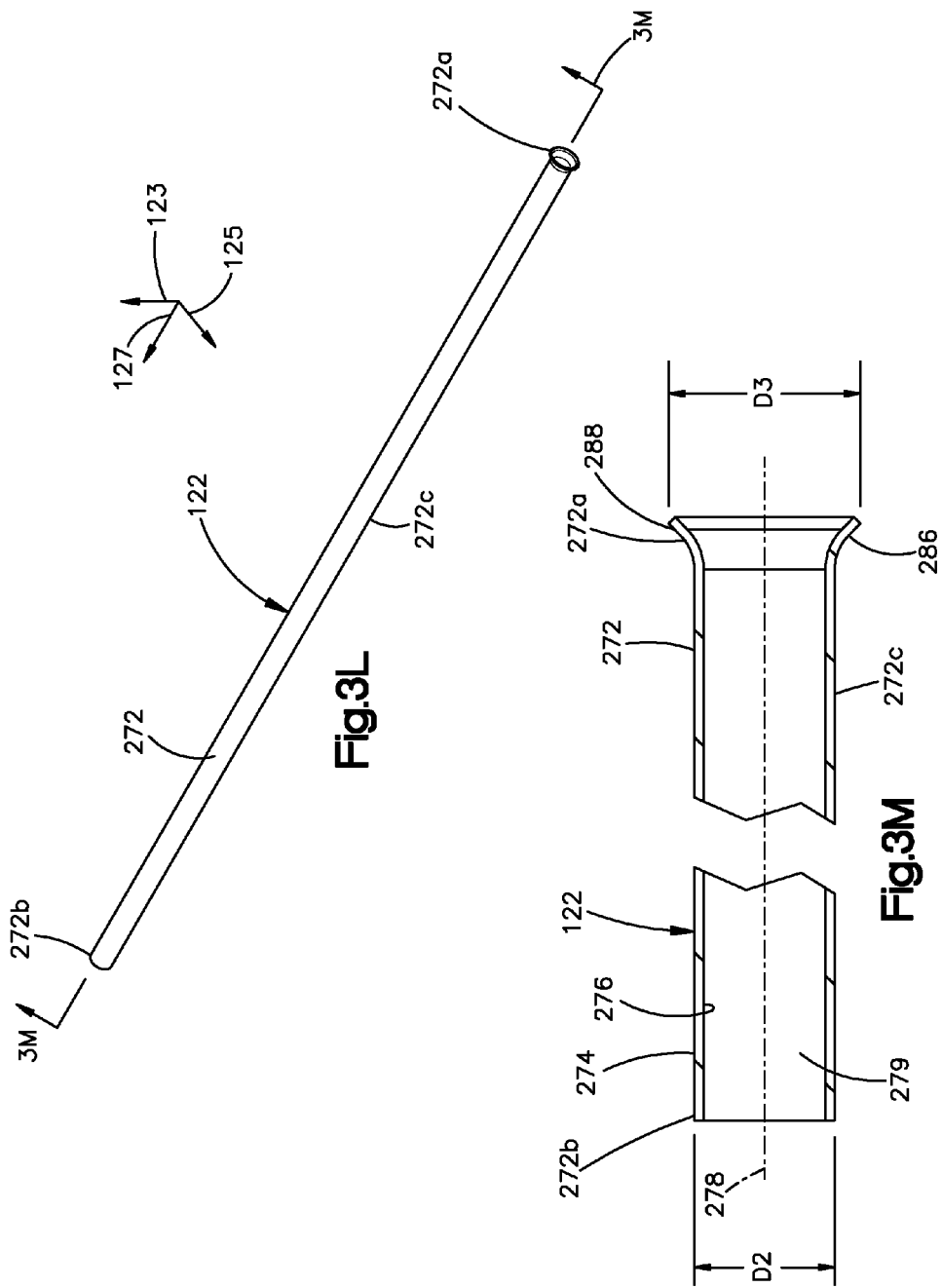

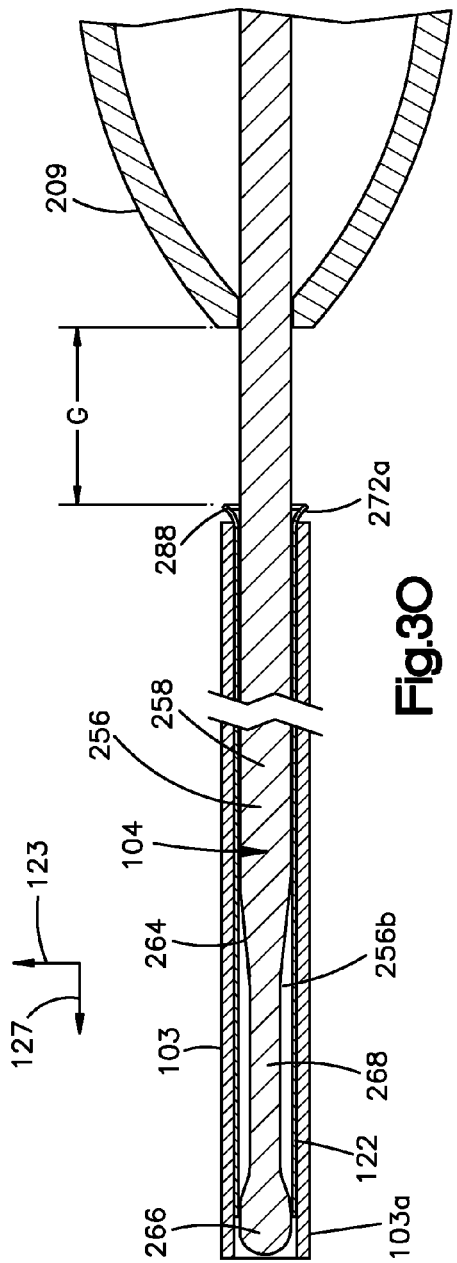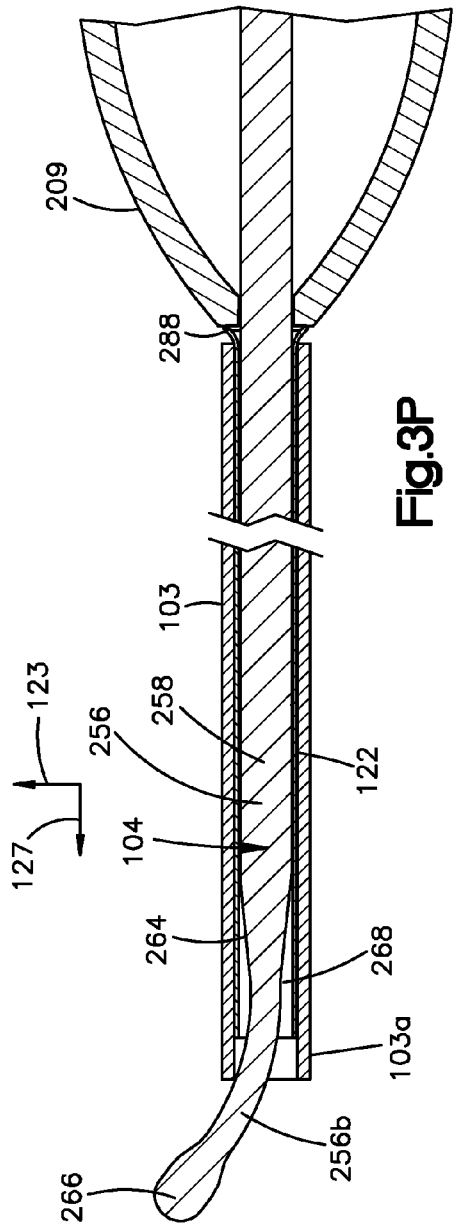

DEVICE TO AID IN THE DEPLOYMENT OF A SHAPE MEMORY INSTRUMENT

TECHNICAL FIELD

The present disclosure relates to apparatus and methods for creating a cavity in tissue, and in particular relates to devices, systems, and methods for creating a cavity in a bone tissue.

BACKGROUND

Vertebral compression fractures ("VCF") involve the collapse of one or more vertebral bodies in the spine, and usually occurs in the lower vertebrae of the thoracic spine or the upper vertebrae of the lumbar spine. The anterior portion of the vertebral body is typically collapsed to a further extent than a posterior portion, resulting in a potentially wedge-shaped, compressed vertebral body, which may result in deformation of the normal alignment or curvature, e.g., lordosis, of the vertebral bodies in the affected area of the spine. VCF and/or related spinal deformities may initiate from, for example, metastatic diseases of the spine, trauma and/or osteoporosis. Until recently, doctors were limited in their treatment options for VCF and related spinal deformities.

One conventional minimally invasive surgical procedure for treating VCF includes a cannula or other access tool that is inserted through the posterior of the targeted vertebral body, usually through the pedicles in such procedures. In one procedure, generally referred to as vertebralplasty, a cannula or bone needle is passed through the soft tissue of the patient's back. Once positioned within the compressed vertebral body, a small amount of polymethylmethacrylate (PMMA) or other orthopedic bone cement is pushed through the needle into the targeted vertebral body. Another such procedure, commonly known as vertebral augmentation, includes the deployment of a mechanical device or expansion of a balloon to create a space in a compressed vertebral body, and a suitable cement, such as polymethylmethacrylate (PMMA) is inserted into the space. Still other conventional procedures involve a first phase of repositioning or restoring the original height of the vertebral body and consequent lordotic correction of the spinal curvature, and a second phase of augmenting, or adding material to the compressed vertebral body, to support or strengthen the compressed vertebral body.

SUMMARY

In accordance with one embodiment, a system is configured to create or enlarge a cavity in a tissue body. The system can include a friction reduction covering that includes a covering body sized to be received in a cannula opening. The friction reduction covering can include an inner covering surface that defines a covering opening that extends through the covering body. The system can further include a cavity creation member that is sized to be at least partially disposed in the covering opening and movable in the covering opening with respect to the cavity creation member from a retracted position to a deployed position whereby the cavity creation member extends out from the friction reduction covering further than when in the retracted position. The cavity creation member can include a portion that is biased to move from a first shape when in the retracted position to a second shape when in the deployed position.

BRIEF DESCRIPTION OF THE DRAWINGS

The foregoing summary, as well as the following detailed description of a preferred embodiment, are better understood when read in conjunction with the appended diagrammatic drawings that illustrate embodiments of the present disclosure. The invention is not limited, however, to the specific instrumentalities disclosed in the drawings. In the drawings:

FIG. 1C is a perspective view of the cannula disposed adjacent the vertebral body after the guidewire has been removed from the vertebral body;

FIG. 2A is a perspective view of the cannula shown in FIG. 1B;

FIG. 2B is a sectional side elevation view of the cannula shown in FIG. 2A, taken along line 2B-B;

FIG. 3A is a perspective exploded view of the cavity creation device shown in FIG. 1E;

FIG. 3B is a perspective view of the cavity creation device illustrated in FIG. 3A, shown in a retracted position;

FIG. 3C is a sectional side elevation view of the cavity creation device shown in FIG. 3B, taken along line 3C-3C;

FIG. 3F is a perspective view of the cavity creation device shown in FIG. 3A, illustrating a cavity creating member in a deployed position;

FIG. 3G is an enlarged sectional side elevation view of a region of the cavity creation device shown in FIG. 3F, taken along line 3G-3G;

FIG. 3L is a perspective view of a friction reduction covering of the cavity creation device shown in FIG. 3A;

FIG. 3M is a sectional side elevation view of the friction reduction covering shown in FIG. 3L, taken along line 3M-3M;

FIG. 3O is an enlarged sectional side elevation view of a portion of the cavity creation device illustrated in FIG. 3N, but shown inserted into the cannula illustrated in FIG. 1C and shown in a retracted position and ready for deployment; and FIG. 3P is an enlarged sectional side elevation view similar to FIG. 3O, but shown in a deployed position.

DETAILED DESCRIPTION OF THE DRAWINGS

Figure 1A:
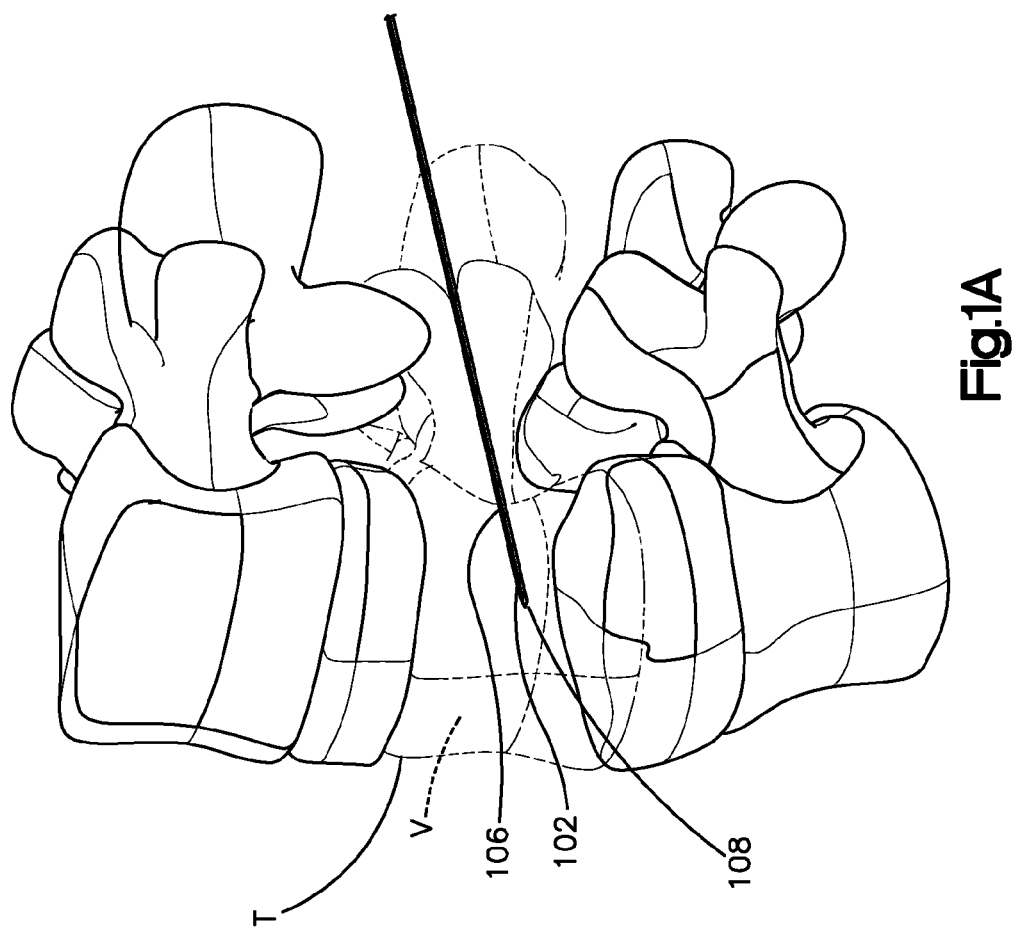
FIG. 1A is a perspective view of a guidewire being inserted into a portion of a vertebral body.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device.

Referring generally to FIGS. 1A-1E, the present disclosure relates to systems and methods for creating a cavity in tissue using minimally invasive techniques. As used herein, the term "tissue" may refer to soft tissue, such as skin, or hard tissue, such as bone tissue. For example, the cavity creation systems can be employed to create a cavity in an anatomical tissue body T such as a vertebral body V. The cavity creation system may include at least one guidewire 102, at least one cannula 103, and at least one cavity creation device 100. As described in more detail below, the cannula 103 can be sized to receive the guidewire 102 and the cavity creation device 100. The guidewire 102 can be introduced into the tissue body T to establish a path toward a target surgical site. The cannula 103 can be introduced over the guidewire 102 to provide a conduit to the target surgical site. Alternatively, the cannula 103 can be inserted and driven to the target surgical site without first inserting the guidewire 102. The cavity creating device 100 can be inserted through the cannula 103 and into the tissue body T to create a cavity in the tissue body T. Specifically, the cavity creation device 100 includes a cavity creation member 104 movable between a first or retracted position and a second or deployed position. Once the cavity creation device 100 is at or near the target surgical site, the cavity creation member 104 can be moved from the retracted position to the deployed position as well as rotated to create a cavity in the tissue body T.

Referring now to FIG. 1A, the guidewire 102 can be configured as a stylet, a K-wire, a guide pin, or any other suitable guide member capable of being introduced into the tissue body T. The guidewire 102 includes a guidewire body 106 that may be made of a substantially rigid material. Further, the guidewire 102 can be made of a substantially rigid material. Suitable materials include, but are not limited to, stainless steel, titanium, and nitinol. The guidewire body 106 may be coated with a material with a relatively low coefficient of friction, such as of polytetrafluoroethylene (PTFE) or silicone, in order to facilitate insertion of the guidewire 102 into the tissue body T. Additionally or alternatively, the guidewire body 106 may be coated with an anticoagulant, such as heparin, or any other medication. The guidewire body 106 may include a distal end 108 that can be tapered so as to facilitate insertion of the guidewire 102 into the tissue body T.

During operation, the guidewire 102 may be introduced into the tissue body T until the distal end 108 reaches the target surgical site. For instance, the target surgical site can be a compressed region in the vertebral body V to which height is to be restored or space is to be created. For example, in the depicted method, the guidewire 102 is introduced through the skin and musculature and into the interior volume of the targeted vertebral body V as shown in FIG. 1A. During insertion, the guidewire 102 can be guided into the tissue body T using any suitable imaging technique such as fluoroscopy or MRI. The guidewire 102 may be introduced, for instance, through one of the pedicles, or directly into the vertebral body (extra-pedicular).

Figure 1B:
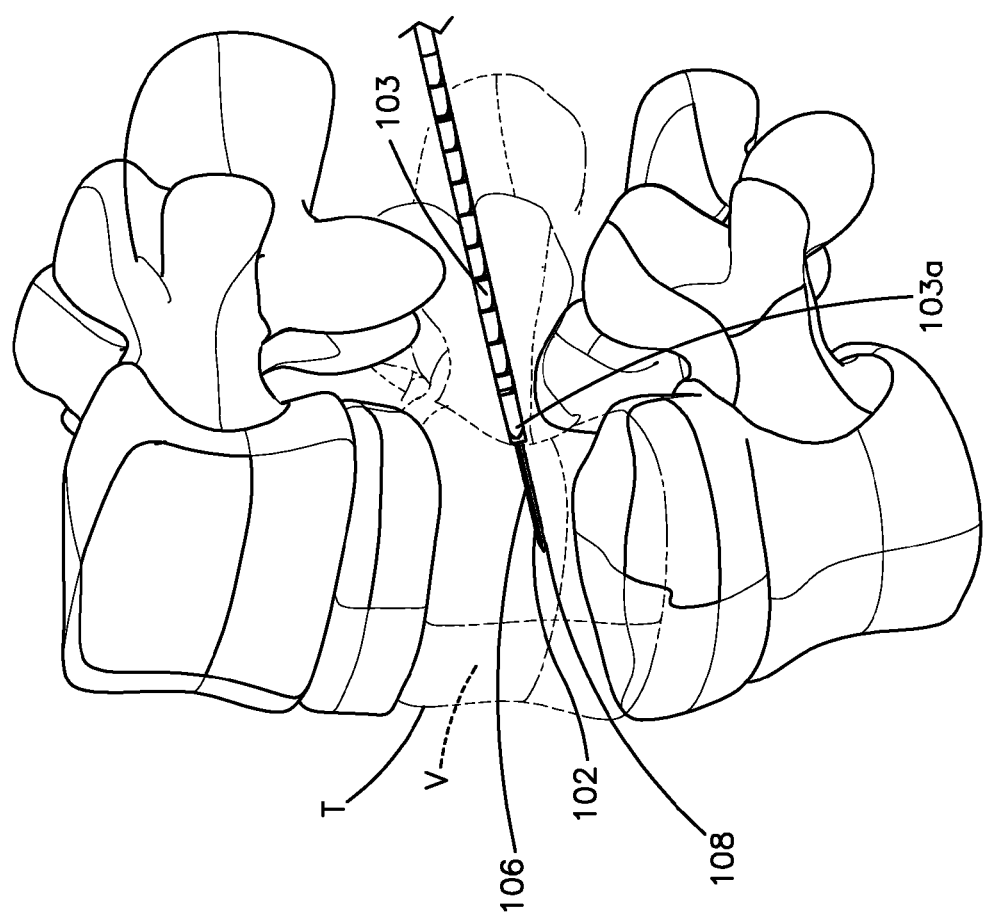
FIG. 1B is a perspective view of a cannula placed over the guidewire that has been inserted in the vertebral body.

Next, referring to FIG. 1B, the cannula 103 defines a distal end 103a that is configured to be positioned adjacent the tissue body T. For instance, the cannula can be translated over the guidewire 102 through the tissue body T, or can be translated through the tissue body T without traveling along a guidewire. Thus, the cannula 103 can be translated toward the target surgical site until the distal end 103a is placed disposed adjacent to an exterior surface of the targeted vertebral body V as shown in FIG. 1B. The guidewire 102, if present, can then be removed from the tissue body T, leaving the cannula 103 in place. For example, the guidewire 102 may be withdrawn from the vertebral body V while leaving the cannula 103 adjacent to the exterior surface of the targeted vertebral body V as shown in FIG. 1C.

Figure 1D:
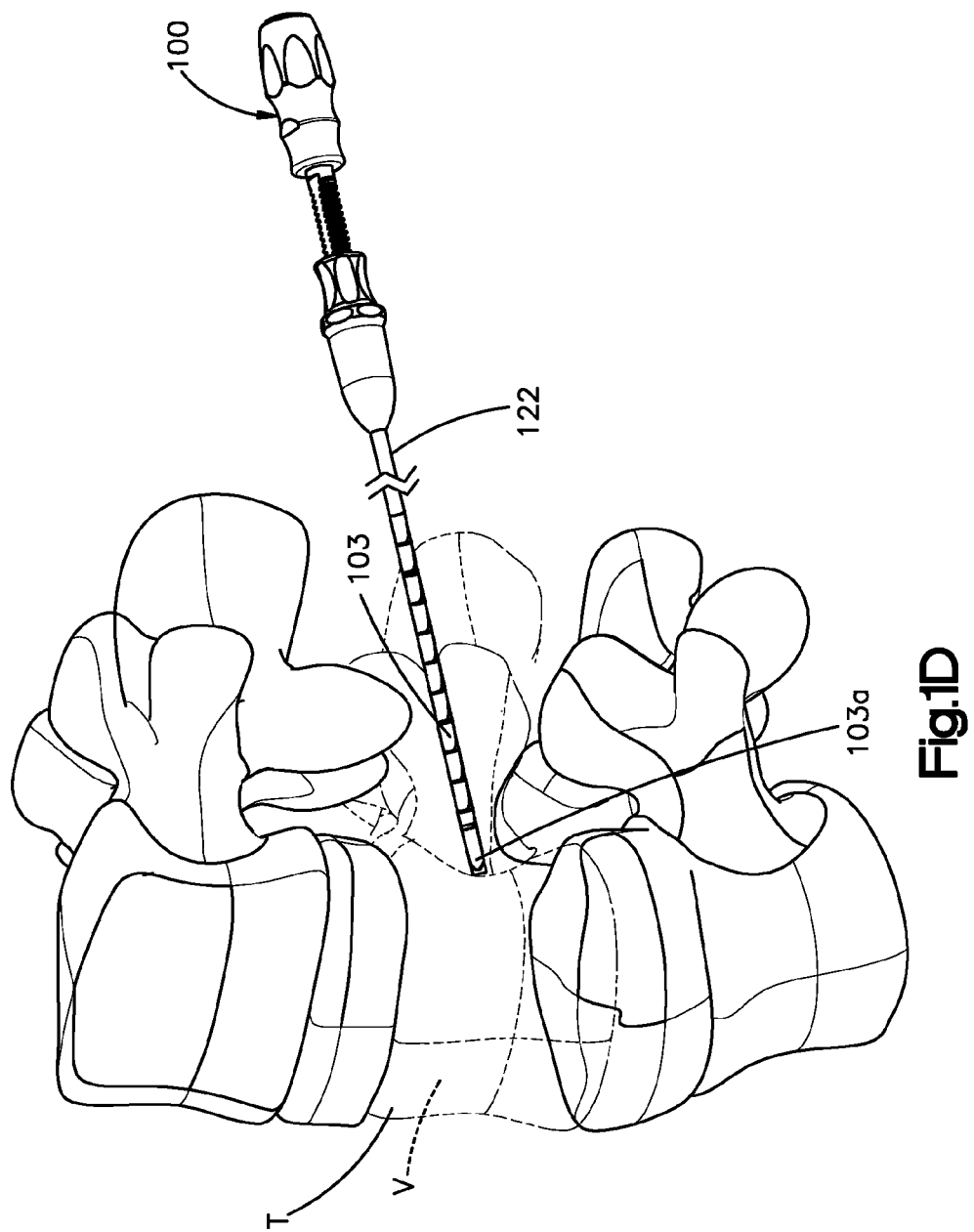
FIG. 1D is a perspective view of the cannula disposed adjacent the vertebral body as shown in FIG. 1C and a cavity creation device at least partially disposed inside the cannula, wherein the cavity creating device includes cavity creation member that is disposed in the retracted position.
Figure 1E:
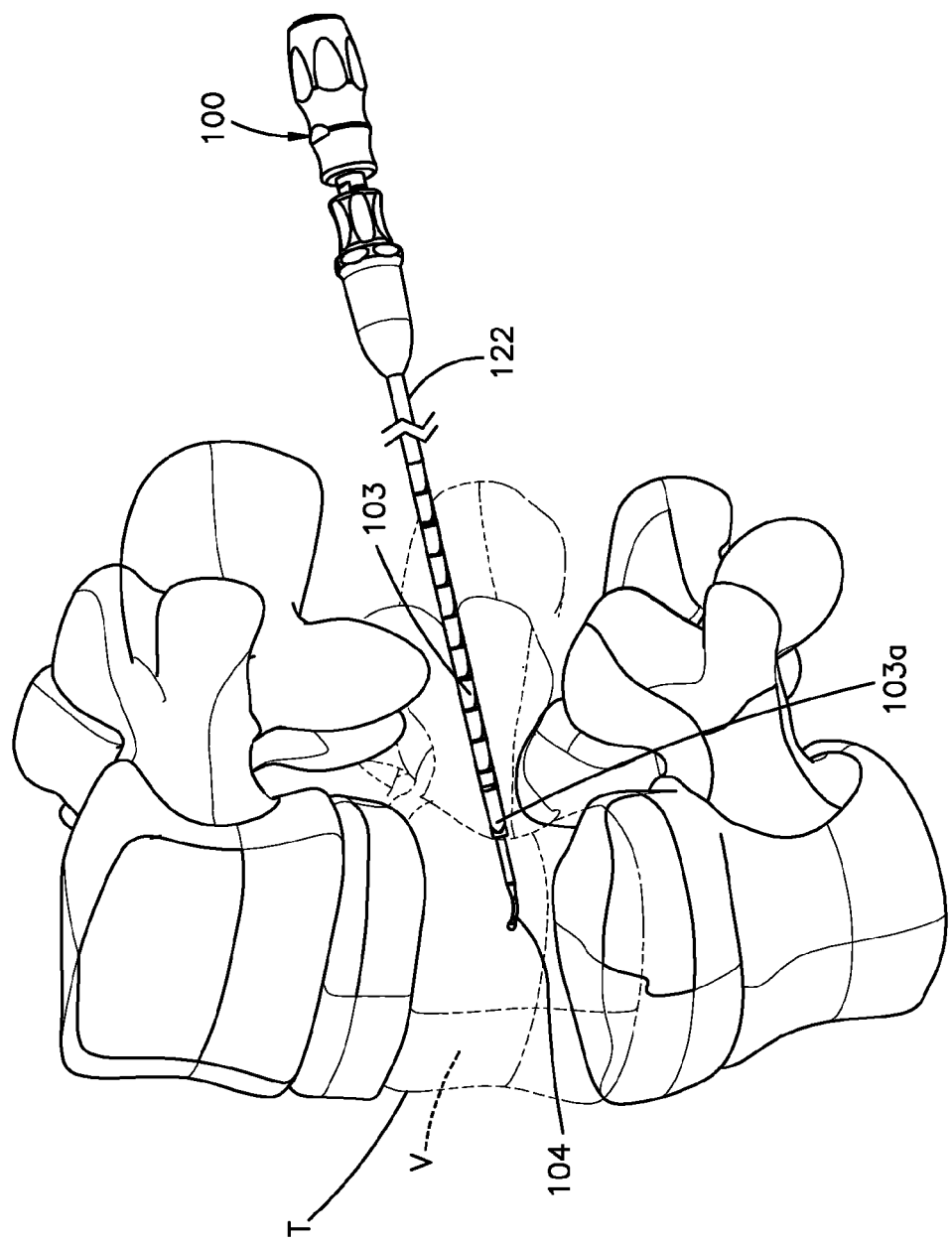
FIG. 1E is a perspective view of the cannula disposed adjacent the vertebral body and the cavity creation device shown in FIG. 1D with the cavity creation member in the deployed position.

Referring to FIG. 1D, at least a portion of the cavity creation device 100 can then be inserted through the cannula 103 toward the distal end 103a of the cannula 103, and thus toward the vertebral body V while the cavity creation member 104 is in the retracted position. In particular, the cavity creation device 100 can be inserted through the cannula 103 such that the distal end of the cavity creation device 100 is substantially aligned with (for instance adjacent) the distal end 103a of the cannula 103 when the cavity creation device 100 is in its retracted position. The cavity creation member 104 can then be moved from the retracted position to the deployed position that is sufficient such that the cavity creation member 104 is configured to create or enlarge a cavity in the tissue body T, such as the vertebral body V. Specifically, moving the cavity creation member 104 from the retracted position to the deployed position causes the distal end of the cavity creation member 104 to be inserted into the vertebral body V, thereby creating a cavity or being inserted into a pre-existing cavity. Rotation of the cavity creation member 104 can cause the cavity to be enlarged.

Referring now to FIGS. 2A-B, the cannula 103 includes a cannula body 110 that may be elongate along a longitudinal direction 114. The cannula body 110 may be made of a substantially rigid material, such as stainless steel, and defines a first or distal end 103a and a second or proximal end 103b that is spaced from the distal end 103a along the longitudinal direction 114. In addition to the distal end 103a and the proximal end 103b, the cannula body 110 defines an outer cannula surface 112 and an inner cannula surface 116 opposite the outer cannula surface 112. The inner cannula surface 116 defines a cannula opening 118 that can be elongated along the longitudinal direction 114 between the distal end 103a and the proximal end 130b, for instance from the distal end 103a to the proximal end 103b. The cannula opening 118 may be configured and sized to selectively receive at least a portion of the guidewire 102 and the cavity creation device 100. The cannula opening 118 may define a first maximum cross-sectional dimension D1. The first maximum cross-sectional dimension D1 may be a diameter. In the depicted embodiment, the cross-sectional dimension of the cannula body 110 can be substantially constant along its length. That is, the cross-sectional dimension of the cannula body 110 can be substantially constant along the longitudinal direction 114. It should be appreciated that the cross-sectional dimension D1 is no smaller than, and can be greater than, that of the guidewire 102, if present, and that of the portion of the cavity creation device 100 that is inserted into the cannula opening 118. For instance, the cross-sectional dimension D1 can be greater than that of the guidewire such that a filler sleeve can be inserted into the cannula 103 so as to narrow the cannula opening 118, such that the guidewire 102 fits snugly inside the cannula 103 as the cannula 103 travels along the guidewire 102. Accordingly, the angular orientation of the guidewire 102 can define the angular orientation of the cannula 103 as the cannula 103 travels along the guidewire 102.

Referring now to FIGS. 3A-C, the cavity creation device 100 is generally elongate along a longitudinal direction 127 between a proximal end P and a distal end D. Thus, reference to a distal direction made with respect to the cavity creation device 100 or components thereof refers to a direction from the proximal end P toward the distal end D. Similarly, reference to a proximal direction made with respect to the cavity creation device 100 or components thereof refers to a direction from the distal end D toward the proximal end P.

Figure 3D:
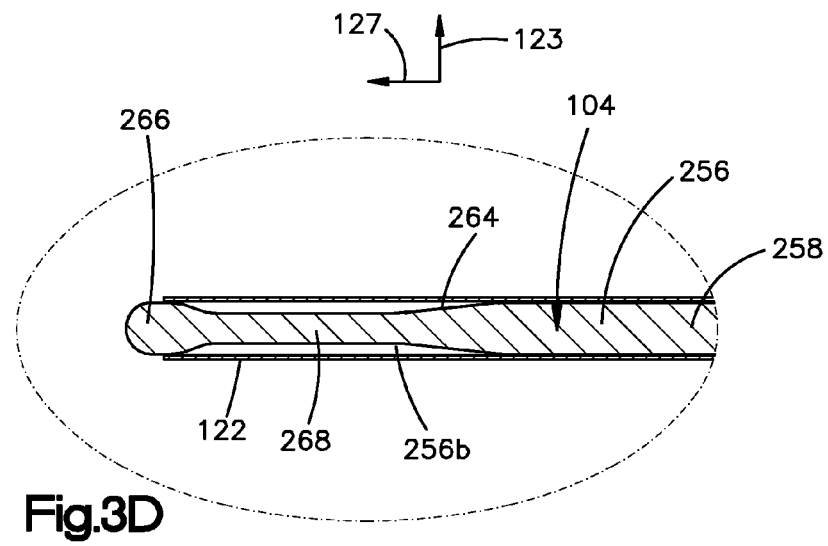
FIG. 3D is an enlarged sectional side elevation view of a region of the cavity creation device shown in FIG. 3A, taken at region 3D and shown in a retracted position.
Figure 3E:
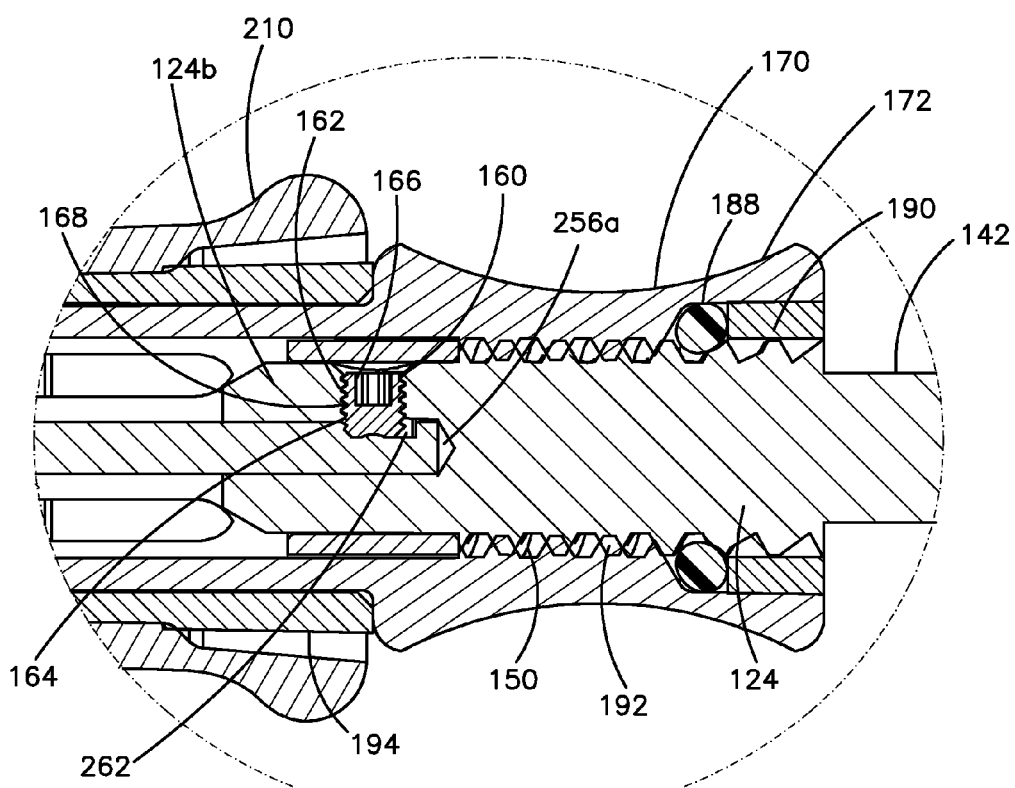
FIG. 3E is an enlarged sectional side elevation view of a region of the cavity creation device shown in FIG. 3A, taken at region 3E.

The cavity creation device 100 includes a body 101, the cavity creation member 104 that extends distally from the body 101, an adjustable stop assembly 120 that is movable along the body 101, and a friction reduction covering 122, such as a sleeve, that is configured to substantially enclose the cavity creation member 104 when the cavity creation member 104 is in the retracted position (see FIG. 3D). When in the deployed position, the cavity creation member 104 extends out from the friction reduction covering 122 further than when in the retracted position. It should be appreciated in some embodiments that the cavity creation member 104 does not extend out from the friction reduction covering 122 when in the retracted position, and that the cavity creation member 104 nevertheless extends out from the friction reduction covering 122 further in the deployed position than when in the retracted position. During operation, the adjustable stop assembly 120 is movable along the body 101, and thus also movable relative to the cavity creation member 104, in the proximal direction away from the friction reduction covering 122 to a retracted position so as to create a gap (see gap G in FIGS. 3N-O) between the friction reduction covering and the adjustable stop assembly 120. The friction reduction covering 122 is then translatable along the proximal direction toward the adjustable stop assembly 120, which causes the distal end of the cavity creation member 104 to extend out the friction reduction covering 122 a sufficient amount for the cavity creation member 104 to change shape, for instance bend, at which point the cavity creation member 104 is in the deployed position (see FIGS. 3F-G).

Thus, when in the retracted position, substantially the entire cavity creation member 104 is disposed within the friction reduction covering 122. Conversely, while in the deployed position, at least an end portion of the cavity creating member 104 is disposed outside the friction reduction covering 122. Thus, it can be said that when the cavity creation member 104 is in the deployed position, the end portion of the cavity creation member 104 is in a position that is distal with respect to the end portion when the cavity creation member is in the retracted position. In accordance with one embodiment, at least a portion of the cavity creation member 104 is configured to be inserted into or otherwise disposed in the cannula opening 118 (see FIG. 2B), such that when the adjustable stop assembly 120 is retracted proximally, movement of the cavity creation device 100, and thus movement of the friction reduction covering 122, along the distal direction with respect to the cannula 103, causes the cannula to bias the friction reduction covering toward the adjustable stop assembly 120, as is described in more detail below. The friction reduction covering 122 can reduce, for instance avoid, direct contact between the cavity creation member 104 and the cannula 103, thereby reducing the friction exerted on the cavity creation member 104 when it moves relative to the cannula 103 between the retraced position and the deployed position.

The body 101 of the cavity creation device 100 can include a handle 126 configured to be grasped by a user, and a drive member 142 that extends distally from the handle 126. The handle 126 may include a handle body 128 that can be knurled or otherwise textured so as to facilitate ergonomically friendly gripping of the handle 126 by the user. The handle body 128 may be elongate along the longitudinal direction 127, and defines a first handle end 132 and a second handle end 134 spaced from the first handle end 132 along the longitudinal direction 127. The handle body 128 further defines a first handle end surface 136 at the first handle end 132 and a second handle end surface 138 at the second handle end 134. The handle 126 may further include a marking 140, such as an arrow, that points or identifies the direction that the end portions of the cavity creation member 104 bends when it is in the deployed position.

The drive member 142 can be configured as a shaft 144, and includes a drive body 146 that is elongate along the longitudinal direction 127. The drive body 146 includes a first or proximal end 124a and a second or distal end 124b that is spaced from the proximal end 124a along the longitudinal direction 127. The proximal end 124a can be coupled to the handle 126, whereas the distal end 124b can be coupled to the cavity creation member 104. For instance, referring to FIG. 3D, the drive member 142 may define a drive hole 160 that extends through the drive body 146 at the distal end 124b, for instance along a transverse direction 123 that is substantially perpendicular to the longitudinal direction 127 and the lateral direction 125. The drive body 146 may define an inner drive surface 162 (see FIG. 3E) that in turn defines the drive hole 160. The drive hole 160 can be configured and sized to receive a set screw 166. The inner drive surface 162, which defines the drive hole 160, may include drive threads 164 that are configured to mate with threads 168 of a set screw 166. The set screw 166 can couple the drive member 142 to the cavity creation member 104 as discussed in detail below. Accordingly, the cavity creation member 104 is fixed with respect to translation relative to the drive member 142 along the longitudinal direction 127. As a result, movement of the adjustable stop assembly 120 relative to the drive member 142 is also relative to the cavity creation member 104.

Referring again to FIGS. 3A-C, the drive body 146 defines an external drive surface 148 and can define external drive threads 150 disposed about at least a portion of the external drive surface 148 that mate with corresponding threads of the adjustable stop assembly 120. Alternatively, the external drive surface 148 can be unthreaded, and the adjustable stop assembly 120 can translate along the external drive surface 148. The external drive surface 148 may include a marker surface 152 that can define a plane that extends along the longitudinal direction 127 and a second direction, such as a lateral direction 125, that is angularly offset, such as substantially perpendicular, with respect to the longitudinal direction L. The drive member 142 can include displacement markings 154 on the marker surface 152. The displacement markings 154 may be spaced from one another along the longitudinal direction 127 and can provide a measurement of the proximal displacement of the adjustable stop assembly 120 with respect to the friction reduction covering 122, and thus the length that the cavity creation member 104 will extend beyond the distal end 103a of the cannula 103.

The adjustable stop assembly 120 includes an actuator 170 movably coupled to the drive member 142, and a stop member 209 that is carried by the actuator. For instance, the stop member 209 can be integral and monolithic with the actuator 170, or attached to the actuator 170 in accordance with the illustrated embodiment. Consequently, the actuation of the actuator 170 causes the actuator 170 and the stop member 209 to move along the longitudinal direction 127 with respect to the drive member 142 and the cavity creation member 104. The actuator 170 can be configured as a knob 172 that, in accordance with the illustrated embodiment, is rotatable with respect to the drive member 142, and thus the cavity creation member 104 and friction reduction covering 122 about a longitudinal rotation axis that can extend along the longitudinal direction 127. Thus, because the actuator 170 is threadedly coupled to the cavity creation member 104, rotation of the actuator 170 about a first direction about the rotation axis causes the adjustable stop assembly 120 to move proximally along the longitudinal direction 127 with respect to the drive member 142, and thus the cavity creation member 104 and friction reduction covering 122. Rotation of the actuator 170 about a second direction about the rotation axis opposite the first direction causes the adjustable stop assembly 120 to move distally along the longitudinal direction 127 with respect to the drive member 142, and thus the cavity creation member 104 and friction reduction covering 122. Alternatively, if the drive member 142 is unthreaded, the actuator 170 can be translated proximally or distally so as to move with respect to the drive member 142, and thus the cavity creation member 104 and friction reduction covering 122, along the longitudinal direction 127.

Figure 3H:
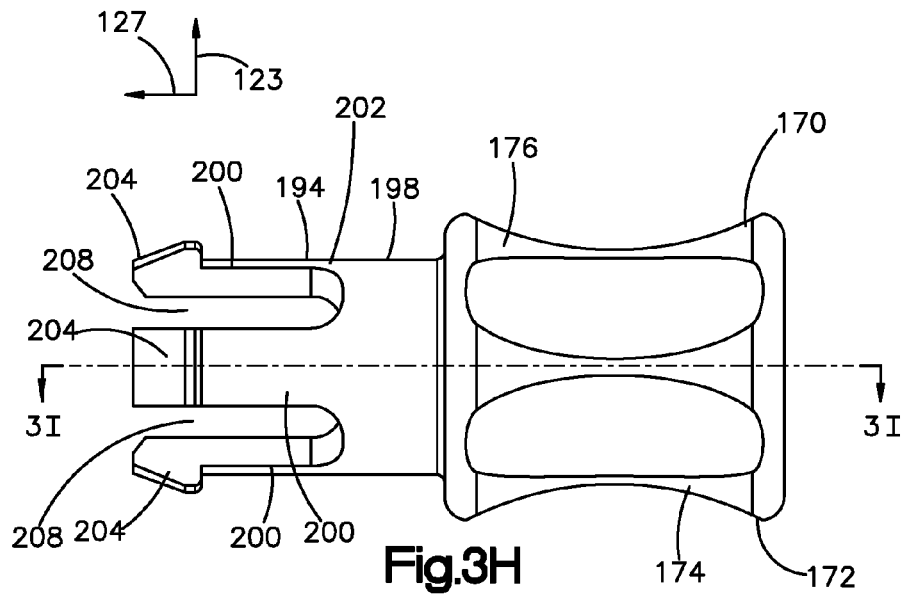
FIG. 3H is a side view of an actuation assembly of the cavity creation device shown in FIG. 3A.
Figure 3I:
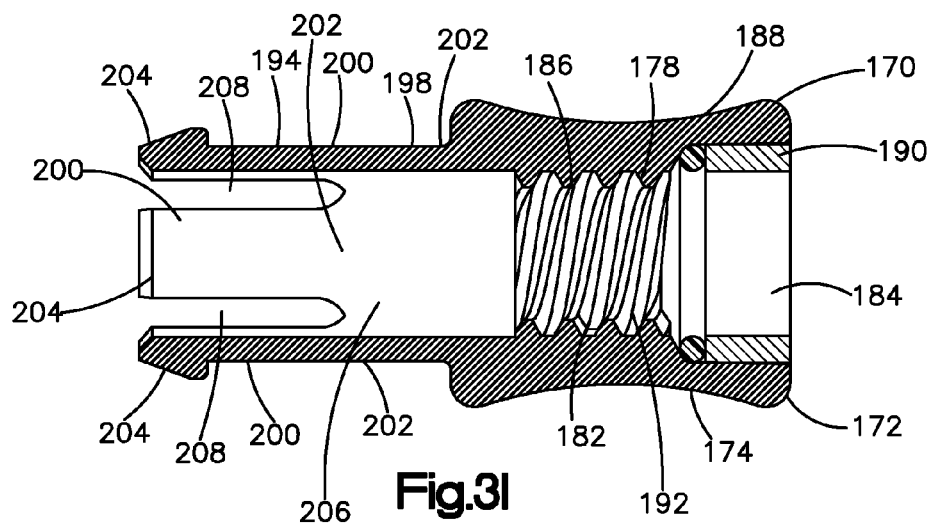
FIG. 3I is a sectional side elevation view of the actuation assembly shown in FIG. 3H, taken along section line 3I-3I.

Referring now to FIGS. 3H-3I, the actuator 170 includes an actuator body 174 that can be made of a substantially rigid material. The actuator body 174 may be elongate along the longitudinal direction 127 and defines an outer actuator surface 176 and an inner actuator surface 178 opposite the outer actuator surface 176. The outer actuator surface 176 can be knurled or otherwise textured so as to facilitate ergonomically friendly gripping of the actuator 170 by the user. The inner actuator surface 178 defines an actuator opening 182 that extends through the actuator body 174. The actuator opening 182 may be elongate along the longitudinal direction 127 and is configured and sized to receive at least a portion of the drive member 142. In the depicted embodiment, the actuator opening 182 defines a first or proximal opening portion 184 and a second or distal opening portion 186 that is spaced from the proximal opening portion 184 along the longitudinal direction 127. The portion of the inner actuator surface 178 that defines the proximal opening portion 184 may or may not include threads. The adjustable stop assembly 120 can further include a seal 188 and a connection sleeve 190 that are sized and configured to be disposed in the actuator opening 182, for instance at the proximal opening portion 184. The actuator opening 182, for instance the proximal opening portion 184, is further configured and sized to receive the drive member 142, such that the seal 188 is disposed between the connection sleeve 190, which can be a retention sleeve, and the distal opening portion 186. The connection sleeve 190 can be coupled to the actuator body 174 by a friction fit connection or any other suitable connection. The seal 188 can be configured as an O-ring or a gasket and functions to prevent or at least inhibit movement of the actuator 170 along the longitudinal direction 127. It should be appreciated that the drive member 142 can be coupled to the actuator 170 in accordance with any suitable alternative embodiment.

The cross-sectional dimension, such as the diameter, of the proximal opening portion 184 may be larger than the cross-sectional dimension of the distal opening portion 186. The portion of the inner actuator surface 178 that defines the distal opening portion 186 may include actuator threads 192 that are configured to mate with the external drive threads 150 of the drive member 142. Consequently, the threaded connection between drive member 142 and the actuator 170 allows the actuator 170 to move longitudinally upon rotation of the actuator 170 relative to the drive member 142 about the rotation axis. In other words, rotating the actuator 170 about the rotation axis with respect to the drive member 142 causes the actuator 170 to move in the longitudinal direction 127. Given that the drive member 142 is coupled to the cavity creation member 104, movement of the actuator 170 with respect to the drive member 142 is also with respect to the cavity creation member 104. Furthermore, because the friction reduction covering 122 is frictionally fit with the cavity creation member 104, movement of the actuator 170 with respect to the cavity creation member 104 in the proximal direction is also with respect to the friction reduction covering 122 in the proximal direction so as to create a gap G (see FIG. 3N).

With continued reference to FIGS. 3A and 3H-3I, the adjustable stop assembly 120 further includes a coupling 234 that is configured to attach the actuator 170 to the stop member 209. The actuator 170 can further include an actuator coupling section 194 that is configured to couple the actuator 170 to the coupling 234. In the depicted embodiment, the actuator coupling section 194 projects distally from the actuator body 174. The actuator coupling section 194 includes a coupling body 198 and a plurality of flexible fingers 200 that project distally from the coupling body 198. The fingers 200 may be spaced from one another along a circumferential path. The actuator coupling section 194 defines a plurality of slots 208 that separate the fingers 200 from one another along the circumferential path. Each finger 200 may be made of a substantially resilient material and defines a first or proximal finger end 202 coupled to the coupling body 198 and a second or distal finger end 204 that is spaced from the proximal finger end 202 along the longitudinal direction 127. The second finger end 204 can be substantially hook-shaped or barbed, or otherwise configured to attach to the coupling 234, as described in more detail below. The actuator 170 further defines an opening 206 that is at least partially aligned with the actuator opening 182 along the longitudinal direction 127. The opening 206 extends through the coupling body 198, and is at least partially defined by the fingers 200 that surround the coupling opening 206. Further, the coupling opening 206 can be configured and sized to receive at least a portion of the drive member 142 and at least a portion of the cavity creation member 104.

Figure 3J:
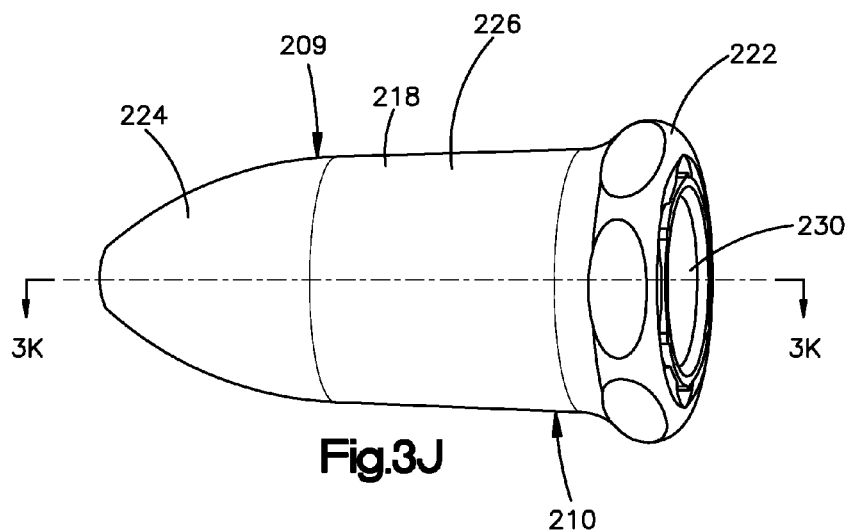
FIG. 3J is a perspective view of a stop assembly of the cavity creation device shown in FIG. 3A.
Figure 3K:
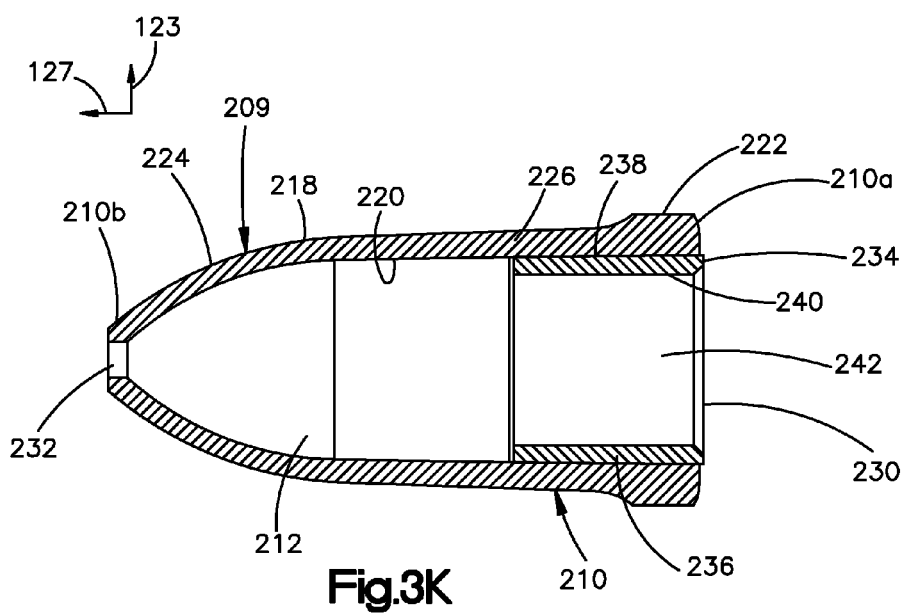
FIG. 3K is a sectional side elevation view of the stop assembly shown in FIG. 3J, taken along line 3K-3K.
Figure 3N:
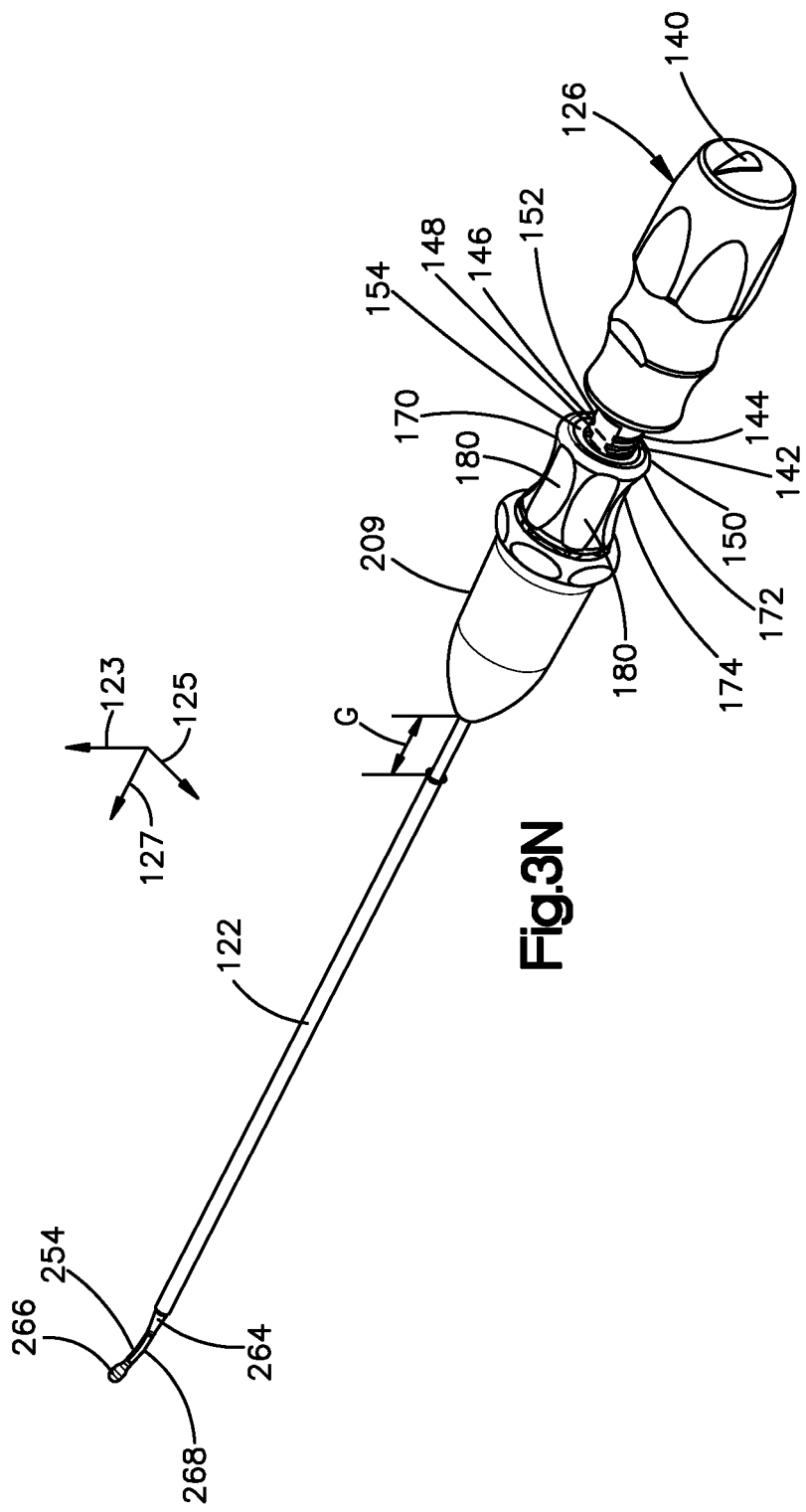
FIG. 3N is a perspective view of the cavity creation device shown in FIG. 3A.

Referring now to FIGS. 3J-3K, the stop member 209 can include a stop body 210 that can be elongate along the longitudinal direction 127. The stop body 210 defines a first or proximal stop end 210a and a second or distal stop end 210b opposite the first stop end 210a. The second stop end 210b may be spaced from the first stop end 210a along the longitudinal direction 127. In the depicted embodiment, the stop body 210 includes a first or proximal stop section 222 disposed adjacent the proximal stop end 210a, a second or distal stop section 224 disposed adjacent the distal stop end 210b, and a third stop section 226 disposed between the proximal and distal stop sections 222 and 224. The proximal stop section 222 can be configured and shaped as a ring or alternatively shaped as desired.

With continued reference to FIGS. 3J-3K, the stop body 210 further defines an outer stop surface 218 and an inner stop surface 220 opposite the outer stop surface 218. The inner stop surface 220 defines a stop opening 212 that extends through the stop body 210 in the longitudinal direction 127. The stop opening 212 can be configured and sized to receive at least a portion of the cavity creating member 104 and at least a portion of the actuator coupling section 194 (see FIG. 3A). The stop body 210 further defines a proximal stop hole 230 that extends longitudinally through the proximal stop end 210a and a distal stop hole 232 that extends longitudinally through the distal stop end 210b, such that the proximal and distal stop holes 230 and 232 are aligned and in communication with the stop opening 212. In the depicted embodiment, the proximal stop hole 230 can be configured and sized to receive at least a portion of the actuator coupling section 194, and the distal stop hole 232 can be configured and sized to receive at least a portion of the cavity creation member 104. Accordingly, the cross-sectional dimension of the proximal stop hole 230 is larger than the cross-sectional dimension of the distal stop hole 232. For instance, the distal stop hole 232 can define a cross-sectional dimension, such as a diameter, that is no less than (for instance substantially equal to) the cross-sectional dimension of the cavity creation member 104.

With continued reference to FIGS. 3J-3K, the coupling 234 is configured to be attached to the stop body 210 in the stop opening 212. The coupling 234 may be disposed closer to the proximal stop end 210a than to the distal stop end 210b. In the illustrated embodiment, the coupling 234 defines an outer coupling surface 238 and an inner coupling surface 240 opposite the outer coupling surface 238. The inner coupling surface 240 can define a coupling opening 242 that extends therethrough along the longitudinal direction 127. The coupling opening 242 can be configured and sized to receive at least a portion of the actuator coupling section 194, such that the distal finger ends 204 extend past the inner coupling surface 240 and the distal finger ends 204 can capture the inner coupling surface 240 so as to attach the stop member 209 to the actuator 170 as shown in FIGS. 3C and 3G.

Referring again to FIG. 3A, and as described above, the cavity creation device 100 includes the cavity creation member 104 that is configured to create or enlarge a cavity in a target location of an anatomical tissue. The cavity creation member 104 can be configured as a wire, a rod, a tube, a shaft, a bar or any other suitable structure capable of creating or enlarging a cavity in anatomical tissue. The cavity creation member 104 includes a member body 256 that can be wholly or partly made of a material having a rigidity sufficient to be inserted through anatomical tissue so as to create or enlarge a cavity in such tissue. For instance, the member body 256 may be wholly or partly made of a metal or a metallic alloy such as a shape memory material of the type described herein. Furthermore, the member body 256 defines a first or proximal member end portion 256a, and a second or distal member end portion 256b, and a middle portion 258 disposed between the proximal and distal end portions 256a-b along the longitudinal direction 127. The member body 256 can define an outer surface 260 that can be shaped as desired, such as substantially cylindrical at the middle portion 258.

Referring now to FIGS. 3D-E, the proximal end 256a of the member body 256 may be coupled to the distal end 124b of the drive body 124. In particular, the set screw 166 or any other suitable coupling apparatus or mechanism may couple the proximal end 256a of the member body 256 to the distal end 124b of the drive body 124. To this end, the proximal end 256a of the member body 256 can define a recess 262 that extends into the member body 256. The recess 262 can be configured and sized to receive at least a portion of the set screw 166. Thus, the set screw 166 can couple the cavity creation member 104 with the drive member 142 when inserted through the drive hole 160 and into the recess 262. It is envisioned, however, that the drive member 142 may be coupled to the cavity creation member 104 using other suitable coupling apparatus or mechanisms, and can further be integral and monolithic with the cavity creation member 104.

With continuing reference to FIG. 3A, at least a portion or an entirety of the member body 256, or portions thereof, may be made of a suitable shape-memory material or any other material with pseudoelastic characteristics. Examples of suitable shape-memory materials include, but are not limited to, suitable shape-memory alloys, such as nickel-titanium alloys (commonly known as nitinol) and shape-memory polymers. In the depicted embodiment, at least the distal end 256b of the member body 256 may be wholly or partly made of a shape-memory material. The distal end 256b is configured to transition between a first shape and a second shape. In accordance with the illustrated embodiment, distal end 256b can have a greater curvature when in the second shape than when in the first shape. Thus, the distal end 256b can extend further outward with respect to the friction reduction covering 122 along a direction that is substantially perpendicular to the longitudinal direction 127 a distance when in the second shape that is greater than when in the first shape. The first shape is illustrated in FIGS. 3B-C, which can be referred to as a substantially straight shape, and the second shape is illustrated in FIG. 3F-G, which can be referred to as a curved shape.

In operation, the distal end 256b may transition from the second shape to the first shape upon application of stress, such that the second shape is the normal shape of the distal end 256b. Conversely, the distal end 256b may transition from the first shape to the second shape upon removal of the applied stress as discussed in detail below. The distal end 256b may include a first or proximal section 264, a second or distal section 266, and a third or intermediate section 268 that is disposed between the proximal and distal sections 264 and 266 along the longitudinal direction 127. The proximal section 264 can be tapered such that its cross-sectional dimension, such as the diameter, decreases in the distal direction. The intermediate section 268 may define a substantially constant cross-sectional dimension, such as the diameter, which can be smaller than that of the distal section 266 and the middle portion 258 of the member body 256. It is envisioned in some embodiments that the intermediate section 268, for instance only the intermediate section 268, is made of a shape-memory material. The distal section 266 can define a shape that is enlarged with respect to the intermediate section 268, for instance can define a round shape. In accordance with one embodiment, the distal section 266 may have a substantially spherical or ellipsoidal shape. Alternatively, the distal section 266 may have a substantially flat shape. Further, it should be appreciated that the intermediate section 268 may have a substantially flat shape.

At least a portion of the cavity creation member 104, including at least a portion of the distal section 266, is configured and sized to be received inside the friction reduction covering 122. In operation, the friction reduction covering 122 maintains the distal end 256b in the first shape, such that the distal end 256b is naturally biased toward the second shape. For instance, mechanical interference between the friction reduction covering 122 and the distal end 256b prevents movement of the distal end 256b from the first shape to the second shape. In the illustrated embodiment (see FIG. 3O), the distal end 256b has a substantially straight shape when it is substantially disposed inside the friction reduction covering 122. Retracting the friction reduction covering 122 from the distal end 256b along the proximal direction causes the distal end 256b to be disposed outside, for instance distal of, the friction reduction covering 122, which causes the distal end 256b to transition from the first shape to the second shape.

Referring now to FIGS. 3L and 3M, the friction reduction covering 122 is configured to move relative to the cavity creation member 104 along the longitudinal direction 127 from a first extending position whereby the cavity creation member 104 is in a retracted position (see FIG. 3D or 3O) to a second retracted position whereby the cavity creation member 104 is in a distracted position (see FIG. 3P). Thus, it should be appreciated that when the friction reduction covering 122 is in the extended position, the cavity creation member 104 is in the retracted position, such that at least a portion of the distal section 266 is disposed within the friction reduction covering 122. It should be further appreciated that when the friction reduction covering 122 is in the retracted position, at least the portion of the distal section 266 extends out from the friction reduction covering 122.

The friction reduction covering 122 can be configured as a sleeve, a tube, or any structure suitable to enclose at least a portion of the cavity creation member 104. In the depicted embodiment, the friction reduction covering 122 is configured as a sleeve and includes a covering body 272 that may be elongate along the longitudinal direction 127. The covering body 272 may have a substantially cylindrical shape and defines an outer covering surface 274 and an inner covering surface 276 that is opposite the outer covering surface 274. The inner covering surface 276 may define covering opening 279 that extends through the covering body 272 along a central opening axis 278, which can extend along the longitudinal direction 127. The covering opening 279 is configured and sized to receive at least a portion of the cavity creation member 104 (FIGS. 3C and 3G) and may be substantially cylindrical in shape, or can define any suitable alternative shape. Thus, the inner covering surface 276 is configured to face and abut the distal end 256b of the cavity creation member 104 when the cavity creation member 104 is in the retracted position.

The covering body 272 includes a first or proximal covering end portion 272a, a second or distal covering end portion 272b spaced proximally from the proximal covering end portion 272a, and a middle covering portion 272c disposed between the proximal end portion 272a and the distal end portion 272b with respect to the longitudinal direction 127. The outer covering surface 274 defines a cross-sectional dimension, such as a diameter, which may vary along the longitudinal direction. For example, the covering body 272 may define a second maximum cross-sectional dimension D2 along the middle covering portion 272c and the distal covering end portion 272b. The cross-sectional dimension D2 of the covering body 272 may remain substantially constant or can vary along the length of the covering body, and in one embodiment is no greater than the cross-sectional dimension D1 of the cannula 103 (FIG. 2B) such that the friction reduction covering 122 can be inserted into the cannula 103.

With continuing reference to FIGS. 3L and 3M, the friction reduction covering 122 can include a stop member, which can be integral with the covering body 272 or can be attached to the covering body 272. In accordance with the illustrated embodiment, the stop member 288 can be defined by the proximal covering end portion 272a. For instance, the stop member 288 can be configured as an enlarged portion 286 or any other structure of mechanism sized and configured to abut the adjustable stop assembly 120, for instance the stop member 209 (see FIG. 3J), so as to define the distance that the cavity creation member 104 extends from the cannula 103. The enlarged portion 286 can flare outward along a direction perpendicular to the longitudinal direction 127, for instance from the proximal portion 272a as it extends along the proximal direction. The enlarged portion 286 can define a third maximum cross-sectional dimension D3, such as a diameter, along the direction that is perpendicular to the longitudinal direction 127 that is larger than the second maximum cross-sectional dimension D2. The third maximum cross-sectional dimension D3 is also larger than the first maximum cross-sectional dimension D1, which is defined by the cannula body 110. As a consequence, when the friction reduction covering 122 extends into the opening 118 of the cannula 103 (see FIG. 2B), the enlarged portion 286 is sized and configured to contact and mechanically interfere with the proximal end 103b of the cannula body 110 so as to prevent further movement of the friction reduction covering 122 relative to the cannula 103 along the proximal direction.

Referring also to FIG. 3A, and as described above, when the friction reduction covering 122 at least partially surrounds the cavity creation member 104, at least a portion of the cavity creation member 104, such as the outer surface 260, bears against the friction reduction covering 122 so as to define a frictional force against the friction reduction covering 112 that resists movement of the friction reduction covering 122 relative to the cavity creation member 104 along the longitudinal direction 127. For instance at least the distal end 256b, and in particular the distal section 266, bears against the friction reduction covering 122, for example against the inner covering surface 276, so as to define the frictional force.

To this end, the covering body 272 may be made of a substantially rigid material with a low coefficient of kinetic friction against the material that defines the cavity creation member 104, such that the frictional force can be easily overcome when it is desired to move the friction reduction covering 122 relative to the cavity creation member 104. In other words, at least the inner covering surface 276 comprises a first material, a portion of the cavity creation member 104, for instance the outer member surface 260 at the distal end 256b, and in particular at the distal section 266, comprises a second material. The first material may exhibit a coefficient of kinetic friction on the second material that ranges as desired. For instance, the friction reduction covering 122 can be inserted into the cannula 103 with minimal friction, and thus under a minimal insertion force (for instance less than five Newtons, and in some instances substantially zero Newtons, until the cannula 103 abuts the enlarged portion 286 of the friction reduction covering 122. Once the friction reduction covering 122 has been inserted into the cannula 103 such that the cannula 103 abuts the enlarged portion 286, the insertion force can increase (for instance to an amount less than 50 Newtons) that is sufficient to overcome a retention force produced by the engagement of the distal section 266 of the cavity creation member 104 and the inner surface of the friction reduction covering 122. Once the retention force has been overcome, the friction reduction covering 122 is free to move along the proximal direction with respect to the cavity creation member 104 a distance equal to the length of the gap G (see FIG. 3N) until the friction reduction covering 122 abuts the stop member 209, which iterates the cavity creation member to the deployed position. Otherwise stated, once the retention force has been overcome, the cavity creation member 104 moves along the distal direction with respect to the friction reduction covering 122 a distance equal to the length of the gap G (see FIG. 3N) until the friction reduction covering 122 abuts the stop member 209.

The inner covering surface 276 may include a lubricious surface. Additionally or alternatively, the covering body 272 may include a lubricious coating. Specifically, at least a portion of the inner covering surface 276, the outer covering surface 274, or both, may be coated with a suitable a lubricious material. Suitable lubricious materials include, but are not limited to, polyetheretherketone (PEEK), polytetrafluoroethylene (PTFE) such as the PTFE sold under the trademark Teflon by Dupont Co., oils, silicon lubricants, bone wax, polyvinylpyrrolidone, Fluorinated Ethylene Propylene (FEP), acrylic polyester, vinyl resin, fluorocarbons, silicone rubber, or combinations of these substances or any other suitable substance capable of defining a predetermined low frictional force between outer member surface 260 of the cavity creation member 104 and the inner covering surface 276 of the friction reduction covering 122. Alternatively or additionally, at least a portion of the outer member surface 260 may be coated with a lubricious material of the type described above.

Referring now to FIGS. 1A-E and FIG. 3N, during operation, a cavity creation system described above can be used to create or enlarge a cavity in the tissue body T. For instance, the cavity creation system can include the cavity creation device 100 and the components thereof, and can further include the cannula 103. The cavity creation system can further include the guidewire 102. Therefore, the cavity creation system can be used as part of a method for creating or enlarging a cavity in the tissue body such as the vertebral body V. This method may include one or more of the following steps. First, the guidewire 102 can be inserted into the tissue body T to establish a path toward the target surgical site. Second, the cannula 103 can be placed over the guidewire 102 and advanced toward the target surgical site in a tissue body. Alternatively, the cannula 103 can be advanced toward the surgical site without the use of the guidewire 102. However, the distal end 103a of the cannula 103 does not need to reach the target surgical site, and can be disposed adjacent the tissue body.

Next, the friction reduction covering 122, which at least partially surrounds at least a portion of the cavity creation member 104, for instance when the cavity creation member is in the retracted position, is inserted distally into the opening 118 of the cannula 103 and advanced toward the target surgical site. Specifically, the cavity creation member 104 may be first disposed inside the friction reduction covering 122, and subsequently, the friction reduction covering 122 and the cavity creating member 104 may be simultaneously disposed or inserted into the cannula 103. Alternatively, the friction reduction covering 122 can first be inserted inside the cannula 103, and, then, the cavity creation member 104 can be inserted distally into the friction reduction covering 122 that is disposed inside the cannula 103, such that the cavity creation member is in the retracted position.

Next, the stop assembly 120 can be moved proximally with respect to the drive member 142, and thus also with respect to the cavity creation member 104 and the friction reduction covering 122. For instance the actuator 170 can be actuated so as to translate proximally with respect to the drive member 142, and thus with respect to the cannula 103 and the cavity creation member 104. For instance, the actuator 170 can be rotated relative to the drive member 142. Because the stop member 209 is attached to the actuator 170, the stop member 209 moves proximally along with the actuator 170, so as to define a gap G (FIG. 3N) that extends along the longitudinal direction 127 between the stop member 209 and the friction reduction covering 122. At this point, the cavity creating member 104 remains in the retracted position due to the frictional force defined between the cavity creating member 104 and the friction reduction covering 122. This friction causes the relative position between the cavity creation member 104 and the friction reduction covering 122 to remain unchanged as the stop assembly 120 moves proximally so as to create the gap G. It should be appreciated as an alternative that the step of creating the gap G can be performed before the friction reduction covering 122 and the cavity creation member are inserted into the cannula 103.

Next, referring also to FIGS. 3O-P, the cavity creation device can be urged to translate distally with respect to the cannula 103, which causes the proximal end 103b of the cannula to bear against the stop member 288 of the friction reduction covering 122 so as to apply a biasing force to the friction reduction covering 122 in the proximal direction. The biasing force can overcome the frictional force between the cavity creation member 104 and the friction reduction covering 122, which thus urges the friction reduction covering 122 to move proximally with respect to the cavity creation member 104, for instance until the proximal end 272a of the friction reduction covering 122 abuts the stop member 209. Thus, the friction reduction covering 122 is free to move proximally relative to the cavity creation member 104 a distance that is substantially equal to the gap G. Otherwise stated, the cavity creation member 104 moves distally relative to the friction reduction covering 122 a distance that is substantially equal to the gap G. In this regard, it should be appreciated that movement of the friction reduction covering 122 relative to the cavity creation member 104 can equally be described with reference to movement of the cavity creation member 104 relative to the friction reduction covering 122. Accordingly, the cavity creation member 104 iterates to the deployed position, whereby the distal end of the cavity creation member 104 extends beyond the distal end of the friction reduction covering 122. Therefore, the cavity creation member 104 is configured to create or enlarge a cavity in the tissue body T such as the vertebral body V.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance with one embodiment can apply to all embodiments as described herein, unless otherwise indicated. Additionally, it should be understood that the concepts described above with the above-described embodiments may be employed alone or in combination with any of the other embodiments described above.

What is claimed:

1. A system configured to create or enlarge a cavity in a tissue body, the system comprising:
    a body defining a proximal body portion including a handle and a distal body portion extending from the proximal body portion in a distal direction, the distal body portion including a distal shaft section;
    an adjustable stop having an internal surface defining an internal bore sized to receive the distal shaft section such that the adjustable stop is translatable along the distal shaft section;
    a friction reduction covering that includes a covering body defining a proximal covering end and a distal covering end spaced from the proximal covering end along the distal direction, the friction reduction covering including an inner covering surface that defines a covering opening that extends through the covering body and the proximal covering end defining a stop member; and
    a cavity creation member having a proximal end portion that extends from the distal body portion in the distal direction, is sized to be at least partially disposed in the covering opening, and is movable in the covering opening with respect to the friction reduction covering from a retracted position to a deployed position, whereby, in the deployed position, the stop member of the friction reduction covering abuts the adjustable stop and the cavity creation member extends out from the friction reduction covering further than when in the retracted position, wherein the cavity creation member includes a portion that is biased to move from a first shape when in the retracted position to a second shape when in the deployed position.

2. The system as recited in claim 1, wherein the inner covering surface comprises a first material, and the cavity creation member defines an outer surface, the outer surface including a second material that is different than the first material.

3. The system as recited in claim 2, wherein the first material is coated onto the covering body.

4. The system as recited in claim 3, wherein at least a portion of the inner covering surface is coated with a lubricious coating that comprises a material selected from the group consisting of polyetheretherketone (PEEK), polytetrafluoroethylene (PTFE), oil, silicon lubricants, fluorinated ethylene propylene, bone wax, polyvinylpyrrolidone, polyurethane, acrylic polyester, vinyl resin, fluorocarbons, silicone rubber, and combinations thereof.

5. The system as recited in claim 1, wherein the cavity creation member defines an end portion that is biased against the inner covering surface of the friction reduction covering when the cavity creation member is in the retracted position, and the end portion extends out the friction reduction covering when the cavity creation member is in the deployed position.

6. The system as recited in claim 5, wherein the friction reduction covering comprises a sleeve that is configured to surround at least the end portion of the cavity creation member.

7. The system as recited in claim 5, wherein the end portion comprises a shape-memory material.

8. The system as recited in claim 1, wherein cavity creation member is more curved when in the second shape than when in the first shape.

9. The system as recited in claim 1, wherein the cavity creation member is configured as a wire that is configured to be inserted into the tissue body.

10. The system as recited in claim 1, wherein the adjustable stop is movable with respect to the cavity creation member so as to define a gap between the adjustable stop and the stop member of the friction reduction covering.

11. The system as recited in claim 10, wherein a biasing force applied to the friction reduction covering urges the friction reduction covering to move relative to the cavity creation member to a position against the adjustable stop, thereby iterating the cavity creation member to the deployed position.

12. The system as recited in claim 11, further comprising a cannula that includes a cannula body and defines a cannula opening that extends through the cannula body, the cannula opening sized to receive the friction reduction covering.

13. The system as recited in claim 12, wherein the cannula is configured to apply the biasing force.

14. The system as recited in claim 13, wherein a portion of the friction reduction covering is positioned so as to mechanically interfere with the cannula, such that movement of the cannula toward the adjustable stop causes the friction reduction covering to travel with the cannula toward the adjustable stop.

15. The system as recited in claim 14, wherein the portion of the friction reduction covering is integral with the covering body.

16. The system as recited in claim 14, wherein the portion of the friction reduction covering is flared.

17. The system as recited in claim 1, wherein the adjustable stop includes an adjustable stop member configured to abut the friction reduction covering and an actuator that is threadedly coupled to a drive member, such that rotation of the actuator about the drive member causes the drive member to move away from the friction reduction covering.

18. The system of claim 1, wherein the cavity creation member is coupled to the body so as to fix the cavity creation member with respect to translation relative to the body along the distal direction and a proximal direction, opposite the distal direction.

19. A system configured to create or enlarge a cavity in a tissue body, the system comprising:
a body defining a proximal body portion including a handle and a distal body portion extending from the proximal body portion in a distal direction, the distal body portion including a distal shaft section;
an adjustable stop having an internal surface defining an internal bore sized to receive the distal shaft section such that the adjustable stop is translatable along the distal shaft section;
a friction reduction covering that includes a covering body defining a proximal covering end and a distal covering end spaced from the proximal covering end along a distal direction, the friction reduction covering including an inner covering surface that defines a covering opening that extends through the covering body and the proximal covering end defining a stop member;
a cavity creation member having a proximal end portion that extends from the distal portion of the body in the distal direction and has an end portion that is sized to be at least partially disposed in the covering opening and movable in the covering opening with respect to the covering opening from a retracted position to a deployed position, wherein the end portion is biased to move from a first shape when in the refracted position to a second shape when in the deployed position and, when in the deployed position, the stop member of the friction reduction covering abuts the adjustable stop and the end portion extends farther from the friction reduction covering than when in the retracted position; and
a cannula that includes a cannula body and defines a cannula opening that extends through the cannula body, wherein the cannula opening is sized to receive the friction reduction covering and configured to bias the friction reduction covering to move relative to the cavity creation member so as to iterate the cavity creation member from the retracted position to the deployed position.

20. The system of claim 19, further comprising a cannula that includes a cannula body and defines a cannula opening that extends through the cannula body, the cannula opening sized to receive the friction reduction covering.

21. The system of claim 20, wherein the cannula is configured to apply a biasing force to the friction reduction covering to urge the friction reduction covering to move relative to the cavity creation member to a position against the adjustable stop, thereby iterating the cavity creation member to the deployed position.

22. The system as recited in claim 19, wherein the cavity creation member is coupled to the body so as to fix the cavity creation member with respect to translation relative to the body along the distal direction and a proximal direction, opposite the distal direction.

23. A system configured to create or enlarge a cavity in a tissue body, the system comprising:
a friction reduction covering that includes a covering body sized to be received in a cannula opening, the friction reduction covering including an inner covering surface that defines a covering opening that extends through the covering body;
a cavity creation member that is sized to be at least partially disposed in the covering opening and movable in the covering opening with respect to the friction reduction covering from a retracted position to a deployed position, whereby the cavity creation member extends out from the friction reduction covering further than when in the retracted position, the cavity creation member including a portion that is biased to move from a first shape when in the retracted position to a second shape when in the deployed position;
a drive member coupled to the cavity creation member;
an adjustable stop movable with respect to the cavity creation member so as to define a gap between the adjustable stop and the friction reduction covering, wherein the cannula is configured to apply a biasing force to the friction reduction covering to urge the friction reduction covering to move relative to the cavity creation member to a position against the adjustable stop, thereby iterating the cavity creation member to the deployed position; and
a cannula that includes a cannula body and defines a cannula opening that extends through the cannula body, the cannula opening sized to receive the friction reduction covering, wherein a portion of the friction reduction covering is positioned so as to mechanically interfere with the cannula, such that movement of the cannula toward the adjustable stop causes the friction reduction covering to travel with the cannula toward the adjustable stop.

24. The system as recited in claim 23, wherein the portion of the friction reduction covering is integral with the covering body.

25. The system as recited in claim 23, wherein the portion of the friction reduction covering is flared.

* * * * *